United States Patent
Hashimoto et al.

(10) Patent No.: US 9,090,577 B2
(45) Date of Patent: Jul. 28, 2015

(54) CATALYST FOR PRODUCING ETHYLENE OXIDE AND METHOD FOR PRODUCING ETHYLENE OXIDE

(75) Inventors: Takaaki Hashimoto, Himeji (JP); Tadashi Sento, Himeji (JP); Masahide Shima, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 802 days.

(21) Appl. No.: 13/262,019

(22) PCT Filed: Mar. 30, 2010

(86) PCT No.: PCT/JP2010/055737
§ 371 (c)(1),
(2), (4) Date: Sep. 29, 2011

(87) PCT Pub. No.: WO2010/113963
PCT Pub. Date: Oct. 7, 2010

(65) Prior Publication Data
US 2012/0022277 A1 Jan. 26, 2012

(30) Foreign Application Priority Data

Mar. 31, 2009 (JP) ................................. 2009-084917
Sep. 25, 2009 (JP) ................................. 2009-220394

(51) Int. Cl.
| | | |
|---|---|---|
| C07D 301/10 | (2006.01) | |
| B01J 21/00 | (2006.01) | |
| B01J 23/00 | (2006.01) | |
| B01J 23/656 | (2006.01) | |
| B01J 23/68 | (2006.01) | |
| B01J 35/10 | (2006.01) | |
| B01J 37/02 | (2006.01) | |
| B01J 37/08 | (2006.01) | |
| B01J 37/12 | (2006.01) | |
| C07D 301/08 | (2006.01) | |
| C07D 303/00 | (2006.01) | |

(52) U.S. Cl.
CPC ............. *C07D 301/10* (2013.01); *B01J 23/002* (2013.01); *B01J 23/6567* (2013.01); *B01J 23/688* (2013.01); *B01J 35/1009* (2013.01); *B01J 35/1038* (2013.01); *B01J 35/1066* (2013.01); *B01J 37/0201* (2013.01); *B01J 37/088* (2013.01); *B01J 37/12* (2013.01); *C07D 301/08* (2013.01); *C07D 303/00* (2013.01); *B01J 2523/00* (2013.01)

(58) Field of Classification Search
CPC .... B01J 23/002; B01J 23/6567; B01J 23/688; B01J 2523/00; B01J 2523/15; B01J 2523/18; B01J 2523/69; B01J 2523/74; B01J 2523/68; B01J 37/12; B01J 37/088; B01J 37/0201; B01J 35/1066; B01J 35/1038; B01J 35/1009; C07D 301/10; C07D 303/00
USPC .................................. 502/241, 243; 549/534
See application file for complete search history.

(56) References Cited

U.S. PATENT DOCUMENTS

| | | |
|---|---|---|
| 2004/0198992 A1 | 10/2004 | Matusz et al. |
| 2008/0281118 A1 | 11/2008 | Matusz |
| 2008/0306289 A1 | 12/2008 | Matusz et al. |

FOREIGN PATENT DOCUMENTS

| | | |
|---|---|---|
| EP | 0266015 A1 | 5/1988 |
| EP | 1517751 | 3/2005 |
| EP | 1955766 | 8/2008 |
| JP | 5-084440 | 4/1993 |
| JP | 9-150058 | 6/1997 |
| JP | 63-126552 | 5/1998 |
| JP | 2005-518276 | 6/2005 |
| JP | 2006-513027 | 4/2006 |
| JP | 2006521927 | 9/2006 |
| JP | 2007-531623 | 11/2007 |
| WO | 2004002954 | 1/2004 |
| WO | 2004/089539 | 10/2004 |

*Primary Examiner* — T. Victor Oh
(74) *Attorney, Agent, or Firm* — Cesari and McKenna, LLP

(57) ABSTRACT

PROBLEM
There is provided a catalyst for producing ethylene oxide which is superior in catalytic selectivity and catalytic life (durability).
SOLUTION
There is provided a catalyst for producing ethylene oxide having a catalyst component supported on a carrier, wherein the carrier has specific surface area of 0.5 to 1.3 $m^2/g$, Si content ($SiO_2$ equivalent) of 0.1 to 5.0% by mass and Na content ($Na_2O$ equivalent) of 0.05 to 1.0% by mass, and the catalyst component is silver (Ag), cesium (Cs), rhenium (Re) and tungsten (W) or molybdenum (Mo).

9 Claims, No Drawings

CATALYST FOR PRODUCING ETHYLENE OXIDE AND METHOD FOR PRODUCING ETHYLENE OXIDE

CROSS REFERENCE TO RELATED APPLICATIONS

This application is a National Stage of International Application No. PCT/JP2010/055737, filed on Mar. 30, 2010, which claims priority to Japanese Application No. 2009-220394 filed Sep. 25, 2009, and Japanese Application No. 2009-084917 filed Mar. 31, 2009. The content of the prior applications are incorporated herein by reference in their entirety.

TECHNICAL FIELD

The present invention relates to a catalyst for producing ethylene oxide and a method for producing ethylene oxide. In more detail, the present invention relates to a catalyst which is superior in selectivity and catalytic life (durability) and capable of producing ethylene oxide in a high selectivity rate over a long period of time, and a method for producing ethylene oxide using this catalyst.

BACKGROUND ART

Production of ethylene oxide by catalytic gas-phase oxidation of ethylene with a molecular-oxygen-containing gas in the presence of a silver catalyst has been widely carried out industrially. As for the silver catalyst to be used in this catalytic gas-phase oxidation, various technologies have been proposed concerning carrier thereof, supporting method, kind and addition amount of reaction accelerator, and the like.

For example, by paying attention to catalyst component, a technology in which catalytic selectivity is improved by using an alkali metal and rhenium in combination as an accelerator has been disclosed (Patent Literatures 1 and 2). Patent Literature 1 discloses a catalyst composition for producing ethylene oxide, comprising rhenium/a compound thereof and other metal such as alkali metal/a compound thereof as a catalyst component, as well as a support having surface area less than 20 $m^2/g$. In addition, Patent Literature 2 discloses a catalyst composition for producing ethylene oxide, comprising silver metal; rhenium, tungsten, molybdenum/a compound thereof; and a component in which a part of rubidium or cesium is substituted by potassium, which are deposited on a carrier having a surface area of 500 $m^2/kg$ or more.

On the other hand, by paying attention to a carrier in the catalysts using silver and rhenium as a catalyst component, a technology to improve activity and selectivity of catalyst has been disclosed (Patent Literature 3). In Patent Literature 3, attention is focused on a point that pores of carrier, in particular, characteristics of pore size distribution and pore volume resulting from pores having a pore size in a specified range play an important role, and there has been disclosed a catalyst comprising a carrier having at least 1 $m^2/g$ of surface area and such pore size distribution that pores having a diameter in a range of 0.2 μm to 10 μm corresponds to at least 70% of the total pore volume, and said pores give at least 0.27 ml/g of pore volume in total to the weight of the carrier; and silver deposited on the carrier in an amount of at least 10 g/kg to the weight of the catalyst.

PRIOR ART LITERATURES

Patent Literatures

Patent Literature 1: JP-A-63-126552 (EP-A-0266015);
Patent Literature 2: JP-A-2006-521927 (WO 2004/089539);
Patent Literature 3: JP-A-2005-518276 (WO 2003/072246).

SUMMARY OF INVENTION

Problem to be Solved by the Invention

In the above-described Patent Literatures 1 and 2, by paying attention to rhenium as a promoter, the subject matter was to improve catalytic selectivity. However, in the catalyst to which rhenium was added, change in oxidation state of rhenium and migration or aggregation of rhenium tended to occur easily, and hence there was a problem in durability of catalyst. Patent Literatures 1 and 2 allege the catalytic selectivity without saying anything on this problem.

In addition, in Patent Literature 3, a carrier having at least 1 $m^2/g$ of surface area and a pore size distribution such that pores with diameters in the range of from 0.2 μm to 10 μm represent at least 70% of the total pore volume is used as a carrier. It should be noted that surface area of carrier is most preferably 1.6 to 2.2 $m^2/g$ (see paragraph [0022]). However, although such a large surface area is effective to support silver, but when rhenium is used as a catalyst component, durability of catalyst remarkably decreases because of migration of the catalyst component and the like. Further, since sequential oxidation reaction of ethylene oxide in fine pores tends to occur easily as pressure becomes higher, a carrier having a high surface frequently fails to provide a high selectivity.

And so, development of a catalyst for producing ethylene oxide which can sufficiently satisfy both of catalytic selectivity and catalytic life (durability) has been demanded, but has not been realized yet.

Therefore, the present invention has been made considering the above-described situation, and is directed to provide a catalyst for producing ethylene oxide which is superior in catalytic selectivity and catalytic life (durability).

In addition, the present invention is also directed to provide a method for producing ethylene oxide by using the above-described catalyst.

Means for Solving the Problem

The present inventors have intensively studied to solve the above problem. As a result, the inventors have found that a catalyst for producing ethylene oxide which can sufficiently satisfy both of selectivity and catalytic life (durability) can be obtained, by controlling specific surface area, silicon (Si) content and sodium (Na) content of a carrier which is used for a catalyst, comprising silver, cesium (Cs), rhenium (Re) and tungsten (W) or molybdenum (Mo) as a catalyst component, within specified ranges, and completed the present invention.

That is, the above-described object can be achieved by a catalyst for producing ethylene oxide having a catalyst component supported on a carrier, wherein the carrier has specific surface area of 0.5 to 1.3 $m^2/g$, Si content ($SiO_2$ equivalent) of 0.1 to 5.0% by mass and Na content ($Na_2O$ equivalent) of 0.05 to 1.0% by mass, and the catalyst component is silver (Ag), cesium (Cs), rhenium (Re) and tungsten (W) or molybdenum (Mo).

In addition, the above-described object can be achieved also by a method for producing ethylene oxide, wherein ethylene is subjected to gas-phase oxidation by molecular-oxygen-containing gas in the presence of the catalyst of the present invention.

Effect of the Invention

The catalyst for producing ethylene oxide of the present invention is superior in selectivity and catalytic life (durability). For this reason, by using the catalyst of the present invention, ethylene oxide can be produced in a high selectivity over a long period of time.

EMBODIMENTS FOR CARRYING OUT THE INVENTION

The present invention provides a catalyst for producing ethylene oxide comprising catalyst component wherein silver (Ag), cesium (Cs), rhenium (Re) and tungsten (W) or molybdenum (Mo) are supported on a carrier having specific surface area of 0.5 to 1.3 $m^2/g$, Si content ($SiO_2$ equivalent) of 0.1 to 5.0% by mass and Na content ($Na_2O$ equivalent) of 0.05 to 1.0% by mass.

In addition, in the present invention, "Si content ($SiO_2$ equivalent) of 0.1 to 5.0% by mass" means that Si content is 0.1 to 5.0% by mass in $SiO_2$ equivalent. In a similar way, "Na content ($Na_2O$ equivalent) of 0.05 to 1.0% by mass" means that Na content is 0.05 to 1.0% by mass in $Na_2O$ equivalent.

Generally, catalytic selectivity and catalytic life are in an incompatible relationship. For this reason, although various studies had been done until now for a catalyst for producing ethylene oxide superior in both of selectivity and catalytic life (durability) as described above, it is present situation that such a catalyst has not been realized yet. Production scale of ethylene oxide is as much as 18 million tons per year. Therefore, for example, by reducing only by 1% in decrease of selectivity after 100 days, amount of ethylene as a raw material to be used is remarkably saved, and an economical effect thereof is very great. Under such circumstance, development of a silver catalyst having more superior catalytic performances (selectivity and durability) has become a consecutive theme for researchers in the art.

In addition, in the field of catalyst, it has been known that catalyst exhibits different performance depending on combination of physical properties and composition of carrier, and kind and amount of catalyst component, and therefore it is difficult to find out a combination which is consistent with the desired performance. Here, a catalyst comprising silver, cesium (Cs) and rhenium (Re) (Ag/Cs/Re catalyst) has an improved selectivity compared with a catalyst comprising silver and Cs (Ag/Cs catalyst). In addition, a catalyst where tungsten (W) or molybdenum (Mo) as an auxiliary accelerator for Re has been added to the above-described catalyst (Ag/Cs/Re/W catalyst or Ag/Cs/Re/Mo catalyst) has an improved selectivity, in particular, improved initial selectivity. However, such Ag/Cs/Re/W or Ag/Cs/Re/Mo catalyst has a very rapid deterioration rate compared with that of the Ag/Cs/Re catalyst which does not comprise W or Mo, and hence has a problem in durability. The inventors of the present application have intensively studied to solve the above-described problem, as a result, have found out a most suitable carrier composition for the Ag/Cs/Re/W or Ag/Cs/Re/Mo catalyst. By using such carrier, deterioration rate can be significantly reduced to improve catalytic life, even in the case of the Ag/Cs/Re/W or Ag/Cs/Re/Mo catalyst.

That is, the catalyst of the present invention comprises silver, cesium (Cs), rhenium (Re) and tungsten (W) or molybdenum (Mo) as catalyst component. Therefore, the catalyst can achieve a superior selectivity. In addition, as a carrier, a carrier having specific surface area of 0.5 to 1.3 $m^2/g$, Si content ($SiO_2$ equivalent) of 0.1 to 5.0% by mass and Na content ($Na_2O$ equivalent) of 0.05 to 1.0% by mass is used. Among the above-described catalyst component, rhenium and tungsten have an action to induce deterioration of catalyst, but by using such carrier, the decrease in catalyst performance can be inhibited • prevented. A mechanism through which such effect can be attained is not clear, but speculated as follows. It should be noted that the present invention is not limited by the following speculation. That is, in the catalyst containing rhenium, during use for a long period of time, migration or aggregation of rhenium and tungsten or molybdenum occurs in the catalyst, or change in state occurs such as change in valence of catalyst component, and catalytic performance decreases. However, when the carrier as described above is used, since the catalyst component is supported on a carrier having comparatively smaller surface area, degree of change of catalyst component during reaction becomes small, and hence decrease in performance can be inhibited. On the other hand, when the surface area becomes too small, there is a problem that sufficient support of catalyst component becomes difficult because dispersibility of the catalyst component decreases. In addition, it is speculated that rhenium interacts with cesium on the catalyst and is present in a form of cesium perrhenate. In fact, when the catalyst was checked, generation of aggregate of cesium perrhenate was frequently observed on the catalyst after reaction. On the contrary, in the case of the carrier relevant to the present invention, it is speculated that by an interaction of silica and sodium in the carrier with cationic component and anionic component in the catalyst, aggregation, migration or change in state of rhenium and tungsten or molybdenum is inhibited, and hence extent of decrease in performance has been reduced.

It should be noted that, in the present description, "rhenium and tungsten or molybdenum" includes all forms of "rhenium and tungsten", "rhenium and molybdenum", as well as "rhenium, tungsten and molybdenum".

Consequently, by using the catalyst for producing ethylene oxide of the present invention, ethylene oxide can be produced in a high selectivity over a long period of time, and the catalyst is industrially very useful.

Hereinafter, embodiments of the present inventions will be explained. It should be noted that, in the description of the present application, "mass" and "weight", "% by mass" and "% by weight", and "parts by mass" and "parts by weight" are synonymous words. Concerning measurement of physical property and the like, measurements are carried out at room temperature (20 to 25° C.)/relative humidity 40 to 50%, unless otherwise noted. Also, "ppm" is "ppm by mass", unless otherwise noted.

In addition, in the present description, "when silver (Ag), cesium (Cs), rhenium (Re) and tungsten (W) are used as catalyst component" and "when silver (Ag), cesium (Cs), rhenium (Re) and molybdenum (Mo) are used as catalyst component" are not distinguished, unless otherwise noted.

In the present invention, carrier composition is not particularly limited, so long as the carrier contains α-alumina as a main component, as well as 0.1 to 5.0% by mass of silicon (Si) in SiO2 equivalent and 0.05 to 1.0% by mass of sodium (Na) in $Na_2O$ equivalent. It should be noted that both of Si content and Na content are based on the total mass of the carrier being 100% by mass. In addition, the carrier "contains α-alumina as a main component" means that content of α-alumina in the carrier is 70% by mass or more (upper limit=100% by mass) to the total mass of the carrier being 100% by mass. The content of α-alumina in the carrier is preferably 90% by mass (upper limit=100% by mass), and more preferably 95% by mass (upper limit=100% by mass). The upper limit of the content of α-alumina to be contained in the carrier is a value calculated by excluding the amounts of Si— and Na-related substances, and corresponds to 99.85% to the total mass of the carrier. In addition, when the carrier is composed only of α-alumina, Si— and Na-related substances, the lower limit of α-alumina is 94.0% to the total mass of the carrier. The carrier may contain other component, so long as it contains α-alumina as a main component as well as Si and Na in the above-described contents. Other component is not particularly limited, but includes, for example, alkali metal (excluding Na), alkaline earth metal as well as oxides thereof, transition metal and oxide thereof, and the like. Contents of these substances are not particularly limited, but content of alkali metal or alkaline earth metal is preferably 0 to 5% by mass, and more preferably 0.01 to 4% by mass in oxides thereof equivalent. Also, content of transition metal is preferably 0.01 to 5% by mass, and more preferably 0.001 to 1.0% by mass in oxides thereof equivalent.

Specific surface area (BET surface area) of the carrier is 0.5 to 1.3 $m^2/g$, and more preferably 0.6 to 1.0 $m^2/g$. By using such carrier, there is an advantage that migration of the catalyst component such as rhenium, tungsten or molybdenum can be inhibited • prevented and decrease in performance can be inhibited, while sufficient amounts of catalyst component can be supported. In addition, specific surface area (BET surface area) of the carrier is further more preferably 0.6 to 0.95 m/g, and particularly preferably 0.65 to 0.95 $m^2/g$. It should be noted that, when specific surface area of the carrier is lower than the above-described lower limit, water absorption rate may not be sufficiently secured and support of catalyst component may become difficult. Contrary, when specific surface area of the carrier exceeds the above-described upper limit, extent of decrease in catalytic performance may become great, because catalyst component migrate due to thermal deterioration and the like and supporting state of the catalyst during reaction tends to be changed compared with that before reaction. It should be noted that, in the present description, "specific surface area" means "BET specific surface area". "BET specific surface area" is measured by B.E.T. method, and specifically it is a value which is measured in the following Examples.

The carrier contains 0.1 to 5.0% by mass of silicon (Si) in $SiO_2$ equivalent to the total mass of the carrier, and by containing silicon in such content, there are advantages that decrease in catalytic performance of rhenium and tungsten or molybdenum can be inhibited • prevented, as well as high selectivity can be stably maintained for a long period of time. The Si content ($SiO_2$ equivalent) in the carrier is more preferably 0.1 to 3.0% by mass, and further more preferably 0.5 to 2.5% by mass to the total mass of the carrier being 100% by mass. It should be noted that, when Si content ($SiO_2$ equivalent) in the carrier is less than the above-described lower limit, a sufficient life stability may not be obtained, and contrary, when the Si content exceeds the upper limit, a high selectivity may not be obtained from the initial stage.

In addition, the carrier contains 0.05 to 1.0% by mass of sodium (Na) in $Na_2O$ equivalent to the total mass of the carrier. By containing sodium in such content, there is an advantage that decrease in catalytic performance can be inhibited • prevented. In addition, the content of sodium is more preferably 0.06 to 0.9% by mass, and further more preferably 0.07 to 0.7% by mass. It should be noted that, when Na content ($Na_2O$ equivalent) in the carrier is less than the above-described lower limit, sufficient life stability may not be obtained, and contrary, when Na content exceeds the upper limit, a high selectivity may not be obtained from the initial stage.

In addition, mass ratio ($SiO_2/Na_2O$ equivalent) of silicon (Si) content ($SiO_2$ equivalent) to sodium (Na) content ($Na_2O$ equivalent) is not particularly limited, but preferably 1 to 100, and more preferably 2 to 30. When the mass ratio is in such a range, selectivity and stability for a long period of time of catalyst can be improved.

It should be noted that the composition of the above-described carrier and content of each component can be determined by using a fluorescent X-ray analysis. More specifically, they can be measured by using RIX 2000 manufactured by Rigaku Corp. as a measurement equipment, by a fundamental parameter method (FP method) or a calibration curve method.

Shape of the carrier is not particularly limited, and includes any one of ring-shaped, spherical, cylindrical and pellet-shaped, besides conventional knowledge can be appropriately referred to. In addition, size (average diameter) of the carrier is not particularly limited, and preferably 3 to 20 mm, and more preferably 4 to 10 mm.

Pore volume of the carrier is also not particularly limited, but preferably 0.1 to 1.0 mL/g, more preferably 0.2 to 0.8 mL/g, and further more preferably 0.3 to 0.6 mL/g. The pore volume of the carrier of 0.1 mL/g or more is preferable because support of catalyst component is easy. On the other hand, the pore volume of the carrier of 1.0 mL/g or less is preferable because strength of the carrier can be secured within a practical range. It should be noted that, as a value of the pore volume of the carrier, a value measured by the mercury intrusion method using a carrier which has been degased at 200° C. for at least 30 minutes as a sample, and Auto Pore III 9420W (manufactured by Shimadzu Corp.) as an measurement equipment, at a pressure in a range of 1.0 to 60,000 psia at 60 measuring points, is employed.

Pore size of the carrier is also not particularly limited, but average pore diameter is preferably 0.1 to 10 μm, more preferably 0.2 to 4.0 μm, and further more preferably 0.3 to 3.0 μm. When average pore diameter is 0.1 μm or more, sequential oxidation of ethylene oxide involved in accumulation of the generated gas during production of ethylene oxide can be inhibited. On the other hand, when average pore diameter is 10 μm or less, strength of the carrier can be secured within a practical range. It should be noted that, as a value of average pore diameter, a value measured by a technique similar to the above-described technique (mercury intrusion method) as a measuring method for pore volume of the carrier, is employed.

Water absorption rate of the carrier is also not particularly limited, but preferably 10 to 70%, more preferably 20 to 60%, and furthermore preferably 30 to 50%. When water absorption rate of the carrier is 10% or more, support of catalyst component becomes easy. On the other hand, when water absorption of the carrier is 70% or less, strength of the carrier can be secured within a practical range. It should be noted that, as a value of water absorption rate of the carrier, a value obtained by the technique which will be described in Examples below, is employed.

The catalyst of the present invention has a constitution where catalyst component comprising at least silver (Ag), cesium (Cs), rhenium (Re) and tungsten (W) or molybdenum (Mo) are supported on the above-described carrier.

It should be noted that, in the present description, "catalyst component comprising at least silver (Ag), cesium (Cs), rhenium (Re) and tungsten (W) or molybdenum (Mo)" includes all forms of "catalyst component comprising silver (Ag), cesium (Cs), rhenium (Re) and tungsten (W)", "catalyst component comprising silver (Ag), cesium (Cs), rhenium (Re) and molybdenum (Mo)", as well as "catalyst component comprising silver (Ag), cesium (Cs), rhenium (Re), tungsten (W) and molybdenum (Mo)".

Among the above-described catalyst component, silver mainly plays a roll of the catalyst active component. Here, content of silver or amount of silver to be supported is not particularly limited, and an effective amount for producing ethylene oxide may be supported. In addition, amount of silver to be supported is not particularly limited, but 1 to 30% by mass, and preferably 5 to 20% by mass based on mass of the catalyst for producing ethylene oxide (based on the total mass of the carrier and the catalyst component, hereinafter, the same as above). When amount of silver to be supported is in such a range, the reaction to produce ethylene oxide by oxidizing ethylene in gas phase with molecular-oxygen-containing gas can be efficiently catalyzed.

In addition, cesium (Cs) and rhenium (Re) generally act as a reaction accelerator of silver. Contents (amounts to be supported) of these substances are not particularly limited, and these substances may be supported each in an amount to be effective for producing ethylene oxide.

Content (amount to be supported) of cesium is not particularly limited, so long as the content is an effective amount for producing ethylene oxide, but 400 to 7000 ppm, preferably 900 to 4500 ppm, and furthermore preferably 1000 to 4000 ppm based on mass of the catalyst for producing ethylene oxide. When the content is in such a range, the reaction to produce ethylene oxide by oxidizing ethylene in gas phase with molecular-oxygen-containing gas can be facilitated effectively. In addition, content of rhenium (Re) (rhenium equivalent) per 1 $m^2/g$ of specific surface area of the carrier is not particularly limited, so long as the content is an effective amount for producing ethylene oxide, but preferably 200 to 1500 ppm, and more preferably 300 to 1400 ppm per 1 $m^2/g$ of specific surface area of the carrier. In addition, content (amount to be supported) of rhenium (Re) is not particularly limited, so long as the content is an effective amount for producing ethylene oxide, but 100 to 1400 ppm, and preferably 200 to 1200 ppm based on mass of the catalyst for producing ethylene oxide. When the content is in such a range, the reaction to produce ethylene oxide by oxidizing ethylene in gas phase with molecular-oxygen-containing gas can be facilitated effectively. In particular, rhenium is considered to be an important element in terms of catalytic selectivity. For this reason, by controlling an amount of rhenium in the above range, catalytic selectivity can be effectively improved. When content of rhenium exceeds the above-described range, not only improvement in selectivity cannot be found, but the content possibly causes adverse effects on life performance because higher reaction temperature is required. In addition, when a higher reaction pressure is employed, it is preferable to increase content (amount to be supported) of rhenium.

Tungsten (W) acts as an auxiliary accelerator for rhenium. Since the catalyst component interacts each other in such way, the catalyst of the present invention can exert a high selectivity. Content (amount to be supported) of tungsten (W) is not particularly limited, and may be supported in an effective amount for producing ethylene oxide. Content (amount to be supported) of tungsten is not particularly limited, but preferably 40 to 1200 ppm, and more preferably 120 to 800 ppm based on mass of the catalyst for producing ethylene oxide. When the content is in such a range, effect of rhenium (effect to improve catalytic selectivity) can be facilitated when ethylene oxide is produced by oxidizing ethylene in gas phase with molecular-oxygen-containing gas.

In the present invention, it has become clear that in particular, weight ratio of rhenium (Re) content to tungsten (W) content is an important factor in terms of improvement in catalytic selectivity. Specifically, the weight ratio of rhenium (Re) content to tungsten (W) content is preferably 0.4 or more and less than 5.0, more preferably 0.5 or more and less than 5.0, further more preferably 0.8 to 4.0, and particularly preferably 1.1 to 3.0. When rhenium and tungsten are supported on the carrier in such a weight ratio, effect of rhenium (effect to improve catalytic selectivity) can be effectively exerted, and therefore, by oxidizing ethylene in gas phase with molecular-oxygen-containing gas in the presence of such catalyst, ethylene oxide can be produced in a high selectivity rate (yield). It should be noted that, in the present description, "weight ratio of rhenium (Re) content to tungsten (W) content" means a weight ratio of content of rhenium in rhenium equivalent to content of tungsten in tungsten equivalent, and also simply referred to as "ratio converted to rhenium/tungsten".

Molybdenum (Mo) acts as auxiliary accelerator for rhenium. Since the catalyst component interacts each other in such way, the catalyst of the present invention can exert a high selectivity. Content (amount to be supported) of molybdenum (Mo) is not particularly limited, and may be supported in an effective amount for producing ethylene oxide. Content (amount to be supported) of molybdenum is not particularly limited, but preferably 10 to 1000 ppm, and more preferably 30 to 800 ppm based on mass of the catalyst for producing ethylene oxide. When the content is in such a range, effect of rhenium (effect to improve catalytic selectivity) can be facilitated when ethylene oxide is produced by oxidizing ethylene in gas phase with molecular-oxygen-containing gas.

In the present invention, it has become clear that in particular, weight ratio of rhenium (Re) content to molybdenum (Mo) content is an important factor in terms of improvement in catalytic selectivity. Specifically, the weight ratio of rhenium (Re) content to molybdenum (Mo) content is preferably 0.4 or more and less than 5.0, and more preferably 0.5 or more and less than 5.0. When rhenium and molybdenum are supported on the carrier in such a weight ratio, effect of rhenium (effect to improve catalytic selectivity) can be effectively exerted, and therefore, by oxidizing ethylene in gas phase with molecular-oxygen-containing gas in the presence of such catalyst, ethylene oxide can be produced in a high selectivity rate (yield). It should be noted that, in the present description, "weight ratio of rhenium (Re) content to molybdenum (Mo) content" means a weight ratio of content of rhenium in rhenium equivalent to content of molybdenum in molybdenum equivalent, and also simply referred to as "ratio converted to rhenium/molybdenum".

Besides the above-described catalyst component, the catalyst of the present invention may contain another catalyst component. Another component is not particularly limited, but includes alkali metal such as lithium, potassium and rubidium (sodium is excluded); alkaline earth metal such as magnesium, calcium, strontium and barium; sulfur, phosphorus, vanadium, chromium, manganese, cobalt, nickel, copper, niobium, molybdenum, tin, antimony, tantalum, bismuth, titanium, zirconium, and the like. In addition, content (amount to be supported) of such another catalyst component is not particularly limited, so long as such component does not inhibit the effect of the catalyst component by the present invention, and preferably 10 to 1000 ppm based on mass of the catalyst for producing ethylene oxide.

The catalyst for producing ethylene oxide of the present invention can be prepared according to the conventional known production method for a catalyst for producing ethylene oxide, except that the carrier as described above is used. Hereinafter, preferable embodiments of the production method for the catalyst of the present invention are described. However, the present invention is not limited to the following preferable embodiments, but the catalyst can be produced by appropriately modifying these embodiments or by using the carrier relevant to the present invention in another known method.

Preparation method of the carrier relevant to the present invention is not particularly limited, but composition of the carrier can be controlled, for example, by employing a preparation method as described below. That is, the method includes: 1) a method where a desired size and amount of pore-forming agent is added to a base powder mainly composed of α-alumina; 2) a method where at least 2 kinds of base powders having different physical properties from each other are blended in a desired mixing ratio; 3) a method where the carrier is calcined at a desired temperature for a desired time; and the like. It should be noted that these methods may be used alone or in an appropriate combination. These preparation methods have been described, for example, in "Properties of porous body and its application technologies", supervised by Yasushi Takeuchi, published by Fuji Techno System (1999). Also, JP-A-1993-329368, JP-A-2001-62291, JP-A-2002-136868, JP Patent No. 2983740, JP Patent No. 3256237, JP Patent No. 3295433, and the like can be referred to. Alternatively, a carrier having a specified composition relevant to the present invention may be obtained by placing order to a manufacturer of carrier.

Hereinafter, preferable embodiments of the preparation method for the carrier relevant to the present invention are described. However, the present invention is not limited to the following preferable embodiments, but the carrier relevant to the present invention can be produced by appropriately modifying these embodiments or according to other known method.

Carrier precursor can be obtained by mixing and sufficiently blending α-alumina powder containing at least α-alumina as a main component, binder, silicon compound as a raw material providing silica, as well as complete burning agent and appropriate amount of water, forming, for example, in a form of spherical, pellet-shaped, or the like by extrusion molding method or the like, drying if necessary, and calcining under the gas atmosphere of inert gas such as helium, nitrogen or argon and/or air or the like.

As the α-alumina powder constituting the above-described carrier containing mainly α-alumina, the one having a purity of 90% or more, preferably 95% or more, further more preferably 99% or more, and particularly preferably 99.5% or more is used. It should be noted that purity may be 100%.

In addition, primary particle diameter of α-alumina is not particularly limited, but preferably 0.01 to 100 μm, more preferably 0.1 to 20 μm, further more preferably 0.5 to 10 μm, and particularly preferably 1 to 5 μm. In addition, secondary particle diameter of the α-alumina powder is preferably 0.1 to 1,000 μm, more preferably 1 to 500 μm, further more preferably 10 to 200 μm, and particularly preferably 30 to 100 μm.

The above-described carrier containing mainly α-alumina may contain, besides this α-alumina powder, aluminum oxide, particularly amorphous alumina, silica, aluminum silicate, mullite, zeolite, and the like (these are collectively referred to as "amorphous alumina and the like"); alkali metal oxide and alkaline earth metal oxide and the like such as potassium oxide, sodium oxide and cesium oxide (these are collectively referred to as "alkali and the like"); and transition metal oxide such as iron oxide and titanium oxide. It should be noted that, in α-alumina powder as a raw material before forming the carrier, sometimes sodium (sodium oxide) is contained although content is very small. In this case, by producing the carrier using the α-alumina powder, a small amount of sodium is contained. For this reason, by confirming a content of sodium in the powder in advance, the carrier can be prepared so that a specified content of sodium can be obtained together with an amount of sodium to be added later. Similarly, it is necessary to select the above-described alumina source while considering the following silicon compound so that the Si content specified by the present invention can be obtained.

The above-described silicon compound includes covalent bond compound such as silicon oxide, silicon nitride, silicon carbide, silane and silicon sulfide; silicates such as sodium silicate, ammonium silicate, sodium aluminosilicate, ammonium aluminosilicate, sodium phosphosilicate and ammonium phosphosilicate; double silicates containing silicon such as feldspar and clay; and silica mixture. Among them, silicon oxide, sodium silicate, double silicate containing silicon such as clay, and the like are preferably used. It should be noted that amount of the silicon compound to be added is adjusted to an amount to be the above-described Si content ($SiO_2$ equivalent).

The above-described binder makes extrusion process easy by providing lubricity. Inorganic binder includes, in particular, alumina gel which is combined with peptizer such as nitric acid and acetic acid. Organic binder includes methylcellulose, ethylcellulose, hydroxyethylcellulose, carboxymethylcellulose, corn starch or alkali metal salt thereof, and the like. Among them, carboxymethylcellulose, sodium carboxymethylcellulose, and the like are preferably used.

Complete burning agent is a material to be added to the mixture which is completely removed from the carrier during calcining so that controlled pores remain in said carrier. These materials include carbonaceous material such as coke, carbon powder, graphite, powdery plastics such as polyethylene, polystyrene and polycarbonate, cellulose and cellulose-based material, and other plant materials such as sawdust, crushed hard nut shell, cashew and walnut. Carbon-based binder can also be useful as a complete burning agent.

The carrier relevant to the present invention can be produced by calcining the carrier precursor obtained in this way under the gas atmosphere of inert gas such as helium, nitrogen, and argon, or air or the like at 1,000 to 1,800° C., and preferably 1,400 to 1,700° C.

Surface area of the carrier may be appropriately adjusted to fall in the range of the present invention, by appropriately selecting surface area of powder containing α-alumina as a main component, binder component, calcining temperature, and the like.

In addition, silica content in the carrier can be calculated from amount of silica contained in the powder containing α-alumina as a main component and silicon compound. Sodium content in the carrier may be adjusted considering amount of sodium contained in silicon compound, organic binder and α-alumina. Furthermore, the sodium content may be adjusted by adding silicon compound and a compound containing sodium to the carrier containing $SiO_2$ and $Na_2O$ obtained in such way, but it is preferable to add silica and sodium compound when the carrier is prepared.

Further, shape of the carrier for the catalyst for producing ethylene oxide of the present invention is not particularly limited, and can be appropriately selected from shapes of the carrier commonly used in preparation of the catalyst for producing ethylene oxide such as, for example, ring-shaped, saddle-shaped, spherical and pellet-shaped, considering industrial points such as pressure loss and strength.

Next, the catalyst for producing ethylene oxide of the present invention is produced using the carrier relevant to the present invention produced as described above. As for production method for the catalyst, the catalyst can be prepared according to the conventional known production method for the catalyst for producing ethylene oxide, except that the carrier as described above is used. Hereinafter, preferable embodiments of the production method for the catalyst of the present invention using the above-described carrier are described. However, the present invention is not limited to the following preferable embodiments, and the catalyst can be produced by appropriately modifying or by using the carrier relevant to the present invention in other known method.

Firstly, precursor of each catalyst component is dissolved in an appropriate solvent to prepare a catalyst precursor solution. Here, the precursor of each catalyst component is not particularly limited, so long as the precursor is in a dissolvable form to a solvent, and includes, for example, in the case of silver, for example, silver nitrate, silver carbonate, silver oxalate, silver acetate, silver propionate, silver lactate, silver citrate, silver neodecanoate, and the like. Among them, silver oxalate and silver nitrate are preferable. Also in the case of rhenium, the precursor includes ammonium perrhenate, sodium perrhenate, potassium perrhenate, perrhenic acid, rhenium chloride, rhenium oxide, cesium perrhenate, and the like. Among them, ammonium perrhenate and cesium perrhenate are preferable. In the case of cesium, the precursor includes nitrate, nitrite, carbonate, oxalate, halide, acetate, sulfate, perrhenate, tungstate, molybdate, and the like of cesium. Among them, cesium nitrate, cesium perrhenate, cesium tungstate and cesium molybdate are preferable. In the case of tungsten, the precursor includes tungsten oxide, paratungstic acid, metatungstic acid, paratungstate, metatungstate, as well as heteropoly acid and/or heteropoly acid salt such as tungstosilicic acid and phosphotungstic acid, and the like. Among them, metatungstic acid, ammonium metatungstate, paratungstic acid, ammonium paratungstate, tungstosilicic acid and phosphotungstic acid are preferable. In the case of molybdenum, the precursor includes molybdenum oxide, molybdic acid, molybdate, as well as heteropoly acid and/or heteropoly acid salt such as silicomolibdic acid and phosphomolybdic acid. Among them, ammonium paramolybdate, cesium paramolybdate, ammonium phosphomolybdate, cesium phosphomolybdate, ammonium silicomolybdate and cesium silicomolybdate are preferable. The above-described catalyst component may be used alone or in a form of a mixture of 2 or more kinds. Further, addition amount of each of the above-described catalyst component may be appropriately determined so that the above-described prescribed catalyst composition is obtained.

The solvent for dissolving the precursor of each of the above-described catalyst component is also not particularly limited, so long as the solvent can dissolve each catalyst component. Specifically, the solvent includes water; alcohols such as methanol and ethanol; aromatic compound such as toluene; and the like. Among them, water and ethanol are preferable.

Here, as for the catalyst precursor solution, besides the above-described catalyst component, a complexing agent to form a complex may be added to a solvent, if necessary. The complexing agent is not particularly limited, and includes, for example, monoethanolamine, diethanolamine, triethanolamine, ethylenediamine, propylenediamine, and the like. The above-described complexing agents may be used alone or in a form of a mixture of 2 or more kinds.

Next, the carrier prepared as described above is impregnated with the catalyst precursor solution thus prepared. In this case, the above-described catalyst precursor solution may be separately prepared for each catalyst precursor, and then, the carrier is sequentially impregnated with each catalyst precursor solution, or the above-described catalyst precursor solution may be prepared by dissolving all catalyst precursors in one solvent as a single catalyst precursor solution, and then, the carrier is impregnated with the single catalyst precursor solution.

Subsequently, the above-described carrier is dried, and then calcined. Drying is preferably carried out in the atmosphere of air, oxygen, or inert gas (for example, nitrogen) at a temperature of 80 to 120° C. Further, the calcining is preferably carried out in the atmosphere of air, oxygen, or inert gas (for example, nitrogen) at a temperature of preferably 100 to 800° C., more preferably 150 to 700° C., further more preferably 100 to 600° C., and particularly preferably 200 to 600° C., for 0.1 to 100 hours, preferably 1 to 20 hours, and more preferably 1 to 10 hours. It should be noted that the calcining may be carried out in only one step, or in 2 or more steps. Preferable calcining conditions include such conditions where 1st step calcining is done in the air atmosphere at 100 to 350° C., and preferably 100 to 250° C. for 0.1 to 10 hours, and 2nd step calcining is done in the air atmosphere at 250 to 450° C. for 0.1 to 10 hours. More preferably, after such calcining in the air atmosphere, a further calcining may be done in an inert gas (for example, nitrogen, helium, argon, and the like) at 450 to 800° C., preferably 450 to 700° C. for 0.1 to 10 hours. By executing such calcining, a catalyst which provides a high selectivity rate from initial stage of reaction and is dramatically superior in catalytic life (durability) can be obtained.

The thus obtained catalyst of the present invention is superior in selectivity and catalytic life (durability). Therefore, by using the catalyst for producing ethylene oxide of the present invention, ethylene oxide can be produced in high selectivity rate over a long period of time, and hence the catalyst is industrially very beneficial.

Consequently, the present invention also provides a method for producing ethylene oxide comprising oxidizing ethylene in gas phase with a molecular-oxygen-containing gas in the presence of the catalyst of the present invention.

The method for producing ethylene oxide of the present invention can be carried out according to the common method except that the catalyst for producing ethylene oxide of the present invention is used as a catalyst.

For example, common conditions in the industrial production scale, that is, reaction temperature of 150 to 300° C., and preferably 180 to 280° C., reaction pressure of 0.2 to 4 MPaG, and preferably 0.5 to 3 MPaG, and space velocity of 1,000 to 30,000 $hr^{-1}$ (STP), and preferably 3,000 to 8,000 $hr^{-1}$ (STP) are employed. Raw material gas to be contacted with the catalyst includes the one composed of 0.5 to 40% by volume of ethylene, 3 to 10% by volume of oxygen, 2 to 30% by volume of carbon dioxide, the balance of inert gas such as nitrogen, argon and steam and lower hydrocarbons such as methane and ethane, and further containing 0.1 to 10 ppm by volume of chlorinated hydrocarbon such as ethyl chloride, ethylene dichloride, vinyl chloride and methyl chloride as a reaction inhibitor. The molecular-oxygen-containing gas to be used in the production method of the present invention includes air, oxygen and enriched air.

It should be noted that the present application is based on JP Application No. 2009-084917 filed on 31 Mar., 2009 and JP Application No. 2009-220394 filed on 25 Sep., 2009, and contents of the disclosures thereof have been incorporated herein in entirety by reference.

EXAMPLES

Effects of the present invention will be explained by means of the following Examples and Comparative Examples. However, the technical scope of the present invention is not limited only to the following Examples. It should be noted that, in the present Examples, various parameters of the carrier were measured by the following procedures.

<Measurement of $SiO_2$, $Na_2O$, Ag, Cs, Re and W Contents in the Carrier>

These contents were measured by fluorescent X-ray analysis. Measurement was carried out using PW 2404 manufactured by Philips as a measurement equipment, by fundamental parameter method (FP method) and calibration curve method.

<Measurement of Specific Surface Area of the Carrier>

A carrier (about 2.0 g) which was crushed and classified to a particle size of 0.85 to 1.2 mm was accurately weighed. The weighed sample was degased at 200° C. for at least 30 minutes, and measured by BET (Brunauer-Emmet-Teller) method.

<Measurement of Water Absorption Rate of the Carrier>

Water absorption rate was measured by the following procedures according to the method described in JIS R 2205 (1998).

a) A carrier before crushing was placed in a dryer maintained at 120° C., and mass was weighed after constant mass was attained (dry mass: W1 (g)).

b) The carrier weighed in the above item a) was immersed under water, and boiled for 30 minutes or longer, then cooled in water at room temperature to prepare a water-saturated sample.

c) The water-saturated sample obtained in the above item b) was taken out from water, the surface was wiped quickly with a wet cloth to remove water droplets, and then weighed (water-saturated sample mass: W2 (g)).

d) Using W1 and W2 obtained in the above, water absorption rate was calculated according to the following Expression 1.

(Expression 1)

$$\text{Water absorption rate } (\%) = \frac{W2 - W1}{W1} \times 100 \quad [\text{Eq. 1}]$$

Example 1

Preparation of Catalyst A

Silver oxalate (14.6 g), cesium nitrate (0.2350 g), ammonium perrhenate (0.0359 g) and ammonium metatungstate (0.0140 g) were dissolved in water (about 10 ml), and further ethylenediamine (6.8 ml) as a complexing agent was added thereto to prepare catalyst precursor solution A.

After carrier A (α-alumina carrier, specific surface area=0.8 $m^2$/g, $SiO_2$ content=1.9% by weight, $Na_2O$=0.19% by weight, water absorption rate=37.1%, pore volume=0.40 mL, average pore diameter=1.98 μm) (52.2 g) was impregnated with this catalyst precursor solution A, carrier A was subjected to a heat treatment in air stream at 300° C. for 0.25 hour. Carrier A was further subjected to a heat treatment in nitrogen stream at 570° C. for 3 hours to obtain catalyst A.

Content of each component of thus obtained catalyst A (based on the catalyst) was as follows: Ag (silver equivalent) =14.8% by mass, Cs (Cs equivalent)=2560 ppm, Re (Re equivalent)=360 ppm, and W (W equivalent)=180 ppm. That is, weight ratio of rhenium (Re) content to tungsten (W) content was about 2 (=360/180), and rhenium content (rhenium equivalent) was 450 ppm per 1 $m^2$/g of carrier specific surface area.

Comparative Example 1

Preparation of Catalyst B

Silver oxalate (14.6 g), cesium nitrate (0.1645 g), ammonium perrhenate (0.0359 g) and ammonium metatungstate (0.0140 g) were dissolved in water (about 10 ml), and further ethylenediamine (6.8 ml) as a complexing agent was added thereto to prepare catalyst precursor solution B.

After carrier B (α-alumina carrier, specific surface area=1.6 $m^2$/g, $SiO_2$ content=0.7% by weight, $Na_2O$=0.02% by weight, water absorption rate=40.0%, pore volume=0.40 mL, average pore diameter=0.91 μm) (52.2 g) was impregnated with this catalyst precursor solution B, carrier B was subjected to a heat treatment in air stream at 300° C. for 0.25 hour. Carrier B was further subjected to a heat treatment in nitrogen stream at 570° C. for 3 hours to obtain catalyst B.

Content of each component of thus obtained catalyst B (based on the catalyst) was as follows, respectively: Ag (silver equivalent)=14.8% by mass, Cs (Cs equivalent)=1790 ppm, Re (Re equivalent)=360 ppm, and W (W equivalent)=180 ppm. That is, weight ratio of rhenium (Re) content to tungsten (W) content was about 2 (=360/180), and rhenium content (rhenium equivalent) was 225 ppm per 1 $m^2$/g of carrier specific surface area.

Comparative Example 2

Preparation of Catalyst C

Silver oxalate (14.6 g), cesium nitrate (0.2136 g), ammonium perrhenate (0.0456 g) and ammonium metatungstate (0.0140 g) were dissolved in water (about 10 ml), and further ethylenediamine (6.8 ml) was added thereto to prepare catalyst precursor solution C.

After carrier C (α-alumina carrier, specific surface area=1.6 $m^2$/g, $SiO_2$ content=2.1% by weight, $Na_2O$=0.18% by weight, water absorption rate=41.2%, pore volume=0.40 mL, average pore diameter=2.75 μm) (52.2 g) was impregnated with this catalyst precursor solution C, carrier C was subjected to a heat treatment in air stream at 300° C. for 0.25 hour. Carrier C was further subjected to a heat treatment in nitrogen stream at 570° C. for 3 hours to obtain catalyst C.

Content of each component of thus obtained catalyst C (based on the catalyst) was as follows, respectively: Ag (silver equivalent)=14.8% by mass, Cs (Cs equivalent)=2320 ppm, Re (Re equivalent)=460 ppm, and W (W equivalent)=180 ppm. That is, weight ratio of rhenium (Re) content to tungsten (W) content was about 2.6 (=460/180), and rhenium content (rhenium equivalent) was 288 ppm per 1 $m^2$/g of carrier specific surface area.

[Evaluation of Catalyst Performance 1]

Catalysts A to C prepared in the above Example 1 and Comparative Examples 1 and 2 were crushed to 600 to 850 μm, respectively. Subsequently, each crushed catalyst (1.2 g) was packed into an external heating type double-tube style stainless steel reactor having inner diameter of 3 mm and tube length of 300 mm. A gas composed of 30% by volume of ethylene, 7.6% by volume of oxygen, 2.1% by volume of carbon dioxide, 3.2 ppm of ethyl chloride, and the balance of nitrogen was introduced into this packed bed, and reaction was carried out under the conditions of reaction pressure of 0.8 MPaG and space velocity of 5500 hr$^{-1}$, so that ethylene conversion amount became 2.5% by volume. Selectivity rates and reaction temperatures at 20th day from initiation of the reaction, and selectivity rates and reaction temperatures at 100th day from initiation of the reaction are shown in Table 1. It should be noted that selectivity rate was calculated according to the following Expression 2. Also, "ethylene conversion amount 2.5% by volume" corresponds to ethylene conversion rate 8.3% (it should be noted that ethylene conversion rate was calculated according to the following Expression 3).

(Expression 2)

$$\text{Selectivity rate (mole \%)} = \frac{\text{(mole number of ethelyne converted to ethylene oxide)}}{\text{(mole number of ethylene reacted)}} \times 100 \quad [\text{Eq. 2}]$$

(Expression 3)

$$\text{Conversion rate (mole \%)} = \frac{\text{(mole number of ethylene reacted)}}{\text{(mole number of ethylene in raw material gas)}} \times 100 \quad [\text{Eq. 3}]$$

by weight, water absorption rate=37.1%, pore volume=0.40 mL, average pore diameter=1.98 μm) (52.2 g) was impregnated with this catalyst precursor solution D, carrier D was subjected to a heat treatment in air stream at 300° C. for 0.25 hour. Carrier D was further subjected to a heat treatment in nitrogen stream at 570° C. for 3 hours to obtain catalyst D. It should be noted that carrier D used in the present Example is the same as carrier A used in Example 1.

Content of each component of thus obtained catalyst D (based on the catalyst) was as follows, respectively: Ag (silver equivalent)=14.8%, Cs (Cs equivalent)=2560 ppm, Re (Re equivalent)=180 ppm, and W (W equivalent)=180 ppm. That is, weight ratio of rhenium (Re) content to tungsten (W) content was about 1 (=180/180), and rhenium content (rhenium equivalent) was 225 ppm per 1 m$^2$/g of carrier specific surface area.

Example 3

Preparation of Catalyst E

Silver oxalate (14.6 g), cesium nitrate (0.2350 g), ammonium perrhenate (0.0718 g) and ammonium metatungstate (0.0140 g) were dissolved in water (about 10 ml), and further ethylenediamine (6.8 ml) was added thereto to prepare catalyst precursor solution E.

After carrier E (α-alumina carrier, specific surface area=0.8 m$^2$/g, SiO$_2$ content=1.9% by weight, Na$_2$O=0.19% by weight, water absorption rate=37.1%, pore volume=0.40

TABLE 1

| | | Carrier | | | | Catalyst component | | | | | 20th day | | 100th day | |
| --- | --- | --- | --- | --- | --- | --- | --- | --- | --- | --- | --- | --- | --- | --- |
| | | | SiO$_2$ | | | Cs | Re | | | | | | | |
| | Catalyst | Specific surface area [m$^2$/g] | content [wt %] | Na$_2$O content [wt %] | SiO$_2$/Na$_2$O | content (based on catalyst) [wtppm] | content (based on catalyst) [wtppm] | W content (based on catalyst) [wtppm] | Re content* [wtppm/(m$^2$/g)] | Re/W weight ratio | Selectivity rate [%] | Reaction temperature [° C.] | Selectivity rate [%] | Reaction temperature [° C.] |
| Example 1 | A | 0.8 | 1.9 | 0.19 | 10 | 2560 | 360 | 180 | 450 | 2 | 91.8 | 255 | 88.5 | 260 |
| Comparative Example 1 | B | 1.6 | 0.7 | 0.02 | 35.0 | 1790 | 360 | 180 | 225 | 2 | 91.5 | 252 | 87.1 | 259 |
| Comparative Example 2 | C | 1.6 | 2.1 | 0.18 | 11.7 | 2320 | 460 | 180 | 288 | 2.6 | 91.6 | 254 | 87.8 | 261 |

*Re content: Rhenium content (equivalent rhenium) per 1 m$^2$/g of carrier specific surface area.

From the above Table 1, it can be understood that catalyst A of the present invention is not only high in selectivity rate at 20th day, but small in degree of decrease in selectivity rate at 100th day compared with those of catalyst B and catalyst C.

Example 2

Preparation of Catalyst D

Silver oxalate (14.6 g), cesium nitrate (0.2350 g), ammonium perrhenate (0.0180 g) and ammonium metatungstate (0.0140 g) were dissolved in water (about 10 ml), and further ethylenediamine (6.8 ml) was added thereto to prepare catalyst precursor solution D.

After carrier D (α-alumina carrier, specific surface area=0.8 m$^2$/g, SiO$_2$ content=1.9% by weight, Na$_2$O=0.19% mL, average pore diameter=1.98 μm) (52.2 g) was impregnated with this catalyst precursor solution E, carrier E was subjected to a heat treatment in air stream at 300° C. for 0.25 hour. Carrier E was further subjected to a heat treatment in nitrogen stream at 570° C. for 3 hours to obtain catalyst E. It should be noted that carrier E used in the present Example is the same as carrier A used in Example 1.

Content of each component of thus obtained catalyst E (based on the catalyst) was as follows, respectively: Ag (silver equivalent)=14.8%, Cs (Cs equivalent)=2560 ppm, Re (Re equivalent)=720 ppm, and W (W equivalent)=180 ppm. That is, weight ratio of rhenium (Re) content to tungsten (W) content was about 4 (=720/180), and rhenium content (equivalent rhenium) was 900 ppm per 1 m$^2$/g of carrier specific surface area.

Example 4

Preparation of Catalyst F

Silver oxalate (14.6 g), cesium nitrate (0.2350 g), ammonium perrhenate (0.0359 g) and ammonium metatungstate (0.07 g) were dissolved in water (about 10 ml), and further ethylenediamine (6.8 ml) was added thereto to prepare catalyst precursor solution F.

After carrier F (α-alumina carrier, specific surface area=0.8 m$^2$/g, SiO$_2$ content=1.9% by weight, Na$_2$O=0.19% by weight, water absorption rate=37.1%, pore volume=0.40 mL, average pore diameter=1.98 μm) (52.2 g) was impregnated with this catalyst precursor solution F, carrier F was subjected to a heat treatment in air stream at 300° C. for 0.25 hour. Carrier F was further subjected to a heat treatment in nitrogen stream at 570° C. for 3 hours to obtain catalyst F. It should be noted that carrier F used in the present Example is the same as carrier A used in Example 1.

Content of each component of thus obtained catalyst F (based on the catalyst) was as follows, respectively: Ag (silver equivalent)=14.8%, Cs (Cs equivalent)=2560 ppm, Re (Re equivalent)=360 ppm, and W (W equivalent)=880 ppm. That is, weight ratio of rhenium (Re) content to tungsten (W) content was about 0.4 (=360/880), and rhenium content (rhenium equivalent) was 450 ppm per 1 m$^2$/g of carrier specific surface area.

Comparative Example 3

Preparation of Catalyst G

Silver oxalate (14.6 g), cesium nitrate (0.2350 g), ammonium perrhenate (0.0359 g) and ammonium metatungstate (0.07 g) were dissolved in water (about 18.3 ml), and further ethylenediamine (6.8 ml) was added thereto to prepare catalyst precursor solution G.

After carrier G (α-alumina carrier, specific surface area=1.4 m$^2$/g, SiO$_2$ content=20.0% by weight, Na$_2$O=0.02% by weight, water absorption rate=60.3%) (41.5 g) was impregnated with this catalyst precursor solution G, carrier G was subjected to a heat treatment in air stream at 300° C. for 0.25 hour. Carrier G was further subjected to a heat treatment in nitrogen stream at 570° C. for 3 hours to obtain catalyst G.

Content of each component of thus obtained catalyst G (based on the catalyst) was as follows, respectively: Ag (silver equivalent)=25.0%, Cs (Cs equivalent)=3210 ppm, Re (Re equivalent)=450 ppm, and W (W equivalent)=220 ppm. That is, weight ratio of rhenium (Re) content to tungsten (W) content was about 2 (=450/220), and rhenium content (rhenium equivalent) was 321 ppm per 1 m$^2$/g of carrier specific surface area.

[Evaluation of Catalyst Performance 2]

In the above-described evaluation of catalyst performance 1, selectivity rates and reaction temperatures of the above-described catalysts D to G at 20th day from initiation of the reaction were measured by the same method under the same conditions as in the above-described evaluation of catalyst performance 1, except that catalysts D to G prepared in Examples 2 to 4 and Comparative Example 3 were used as a catalyst instead. The results are shown in Table 2.

TABLE 2

| | | Carrier | | | | Catalyst component | | | | | 20$^{th}$ day | |
|---|---|---|---|---|---|---|---|---|---|---|---|---|
| | Catalyst | Specific surface area [m$^2$/g] | SiO$_2$ content [wt %] | Na$_2$O content [wt %] | SiO$_2$/Na$_2$O | Cs content (based on catalyst) [wtppm] | Re content (based on catalyst) [wtppm] | W content (based on catalyst) [wtppm] | Re content* [wtppm/(m$^2$/g)] | Re/W weight ratio | Selectivity rate [%] | Reaction temperature [° C.] |
| Example 2 | D | 0.8 | 1.9 | 0.19 | 10 | 2560 | 180 | 180 | 225 | 1 | 89.1 | 251 |
| Example 3 | E | 0.8 | 1.9 | 0.19 | 10 | 2560 | 720 | 180 | 900 | 4 | 89.2 | 275 |
| Example 4 | F | 0.8 | 1.9 | 0.19 | 10 | 2560 | 360 | 880 | 450 | 0.4 | 88.4 | 278 |
| Comparative Example 3 | G | 1.4 | 2.0 | 0.02 | 1000 | 3210 | 450 | 220 | 321 | 2 | 84.0 | 254 |

*Re content: Rhenium content (rhenium equivalent) per 1 m$^2$/g of carrier specific surface area.

Example 5

Preparation of Catalyst H

Silver oxalate (14.6 g), cesium nitrate (0.1709 g), ammonium perrhenate (0.0456 g) and ammonium metatungstate (0.0140 g) were dissolved in water (about 10 ml), and further ethylenediamine (6.8 ml) was added thereto to prepare catalyst precursor solution H.

After carrier H (α-alumina carrier, specific surface area=0.8 m$^2$/g, SiO$_2$ content=0.7% by weight, Na$_2$O=0.12% by weight, water absorption rate=41%, pore volume=0.42 mL, average pore diameter=2.1 μm) (52.2 g) was impregnated with this catalyst precursor solution H, carrier H was subjected to a heat treatment in air stream at 300° C. for 0.25 hour. Carrier H was further subjected to a heat treatment in nitrogen stream at 570° C. for 3 hours to obtain catalyst H.

Content of each component of thus obtained catalyst H (based on the catalyst) was as follows, respectively: Ag (silver equivalent)=14.8%, Cs (Cs equivalent)=1860 ppm, Re (Re equivalent)=460 ppm, and W (W equivalent)=180 ppm. That is, weight ratio of rhenium (Re) content to tungsten (W) content was about 2.6 (=460/180), and rhenium content (rhenium equivalent) was 575 ppm per 1 m$^2$/g of carrier specific surface area. Characteristics of catalyst H used in Example 5 are summarized in Table 3.

[Evaluation of Catalyst Performance 1]

Similarly to catalysts A to C, evaluation of catalyst performance for catalyst H was also carried out in the same way as in evaluation of catalyst performance 1 (Table 4).

TABLE 3

|  |  | Specific surface area [m²/g] | SiO₂ content [wt %] | Na₂O content [wt %] | SiO₂/ Na₂O | — |
|---|---|---|---|---|---|---|
|  | Carrier | 0.8 | 0.7 | 0.12 | 5.8 | — |
|  |  | Cs content (based on catalyst) [wtppm] | Re content (based on catalyst) [wtppm] | W content (based on catalyst) [wtppm] | Re content* [wtppm/ (m²/g)] | Re/W weight ratio |
| Example 5 Catalyst H | Catalyst component | 1860 | 460 | 180 | 575 | 2.6 |

*Re content: Rhenium content (rhenium equivalent) per 1 m²/g of carrier specific surface area.

TABLE 4

|  |  | 20th day | | 100th day | |
|---|---|---|---|---|---|
|  | Catalyst | Selectivity rate [%] | Reaction temperature [° C.] | Selectivity rate [%] | Reaction temperature [° C.] |
| Example 5 | H | 91.8 | 253 | 88.4 | 259 |

Example 6

Preparation of Catalyst I

Silver oxalate (14.6 g), cesium nitrate (0.1709 g), ammonium perrhenate (0.0555 g) and ammonium metatungstate (0.0280 g) were dissolved in water (about 10 ml), and further ethylenediamine (6.8 ml) was added thereto to prepare catalyst precursor solution I.

After carrier I (α-alumina carrier, specific surface area=0.8 m²/g, SiO₂ content=0.7% by weight, Na₂O=0.12% by weight, water absorption rate=41%, pore volume=0.42 mL, average pore diameter=2.1 μm) (52.2 g) was impregnated with this catalyst precursor solution I, carrier I was subjected to a heat treatment in air stream at 300° C. for 0.25 hour. Carrier I was further subjected to a heat treatment in nitrogen stream at 570° C. for 3 hours to obtain catalyst I.

Content of each component of thus obtained catalyst I (based on the catalyst) was as follows, respectively: Ag (silver equivalent)=14.8%, Cs (Cs equivalent)=1860 ppm, Re (Re equivalent)=550 ppm, and W (W equivalent)=350 ppm. That is, weight ratio of rhenium (Re) content to tungsten (W) content was about 1.6 (=550/350), and rhenium content (rhenium equivalent) was 688 ppm per 1 m²/g of carrier specific surface area. Characteristics of catalyst I used in Example 6 are summarized in Table 5.

[Evaluation of catalyst performance 3]

Catalyst I prepared in Example 6 was crushed to 600 to 850 μm, respectively. Subsequently, each crushed catalyst (1.2 g) was packed into an external heating type double-tube style stainless steel reactor having inner diameter of 3 mm and tube length of 300 mm. A gas composed of 23% by volume of ethylene, 7.6% by volume of oxygen, 2.1% by volume of carbon dioxide, 2.6 ppm of ethyl chloride, the balance of nitrogen was introduced into this packed bed, and reaction was carried out under the conditions of reaction pressure of 1.6 MPaG and space velocity of 5500 hr⁻¹, so that ethylene conversion amount became 2.5% by volume. Selectivity rate and reaction temperature at 5th day from initiation of the reaction and selectivity rate and reaction temperature at 40th day from initiation of the reaction are shown in Table 6. It should be noted that selectivity rate was calculated according to the Expression 2. Also, "ethylene conversion amount 2.5% by volume" corresponds to ethylene conversion rate 10.9% (it should be noted that ethylene conversion rate was calculated according to the Expression 3).

TABLE 5

|  |  |  | Specific surface area [m²/g] | SiO₂ content [wt %] | Na₂O content [wt %] | SiO₂/ Na₂O | — |
|---|---|---|---|---|---|---|---|
|  |  | Carrier | 0.8 | 0.7 | 0.12 | 5.8 | — |
|  |  |  | Cs content (based on catalyst) [wtppm] | Re content (based on catalyst) [wtppm] | W content (based on catalyst) [wtppm] | Re content* [wtppm/ (m²/g)] | Re/W weight ratio |
| Example 6 | Catalyst I | Catalyst component | 1860 | 550 | 350 | 688 | 1.6 |

*Re content: Rhenium content (rhenium equivalent) per 1 m²/g of carrier specific surface area.

TABLE 6

|  |  | Initial stage of reaction | | 40th day | |
|---|---|---|---|---|---|
|  | Catalyst | Selectivity rate [%] | Reaction temperature [° C.] | Selectivity rate [%] | Reaction temperature [° C.] |
| Example 6 | I | 88.5 | 252 | 88.3 | 255 |

Example 7

Preparation of Catalyst J

Hereinafter, procedures for preparing catalyst J are shown. Silver oxalate (14.6 g), cesium nitrate (0.1923 g), ammonium perrhenate (0.0359 g) and ammonium paramolybdate tetrahydrate (0.0107 g) were dissolved in water (about 10 ml), and further ethylenediamine (6.8 ml) as a complexing agent was added thereto to prepare catalyst precursor solution J.

Carrier J (α-alumina carrier, specific surface area=0.85 $m^2/g$, $SiO_2$ content=1.91% by mass, $Na_2O$=0.19% by mass, water absorption rate=37.1%, pore volume=0.40 ml/g, average pore diameter=1.98 μm) (52.2 g) was impregnated with this catalyst precursor solution J, and then dried at 90° C. under reduced pressure. Carrier J was subjected to a heat treatment in air stream at 300° C. for 0.25 hour, then further subjected to a heat treatment in nitrogen stream at 570° C. for 3 hours to obtain catalyst (J).

Content of each component of thus obtained catalyst (J) (based on mass of the catalyst) was as follows: Ag (silver equivalent)=14.8% by mass, Cs (Cs equivalent)=2180 ppm by mass, Re (Re equivalent)=360 ppm by mass, and Mo (Mo equivalent)=90 ppm by mass. That is, weight ratio of rhenium (Re) content to molybdenum (Mo) content was about 4.0 (=360/90), and rhenium content (rhenium equivalent) was 424 ppm per 1 $m^2/g$ of carrier specific surface area.

Example 8

Preparation of Catalyst K

Hereinafter, procedures for preparing catalyst K are shown. Silver oxalate (14.6 g), cesium nitrate (0.1710 g), ammonium perrhenate (0.0457 g) and ammonium paramolybdate tetrahydrate (0.0213 g) were dissolved in water (about 10 ml), and further ethylenediamine (6.8 ml) as a complexing agent was added thereto to prepare catalyst precursor solution K.

Carrier K (α-alumina carrier, specific surface area=0.93 $m^2/g$, $SiO_2$ content=0.65% by mass, $Na_2O$=0.12% by mass, water absorption rate=40.1%, pore volume=0.42 ml/g, average pore diameter=2.1 μm) (52.2 g) was impregnated with this catalyst precursor solution K, and then dried at 90° C. under reduced pressure. Carrier K was subjected to a heat treatment in air stream at 300° C. for 0.25 hour, then further subjected to a heat treatment in nitrogen stream at 570° C. for 3 hours to obtain catalyst (K).

Content of each component of thus obtained catalyst (K) (based on mass of the catalyst) was as follows: Ag (silver equivalent)=14.8% by mass, Cs (Cs equivalent)=1940 ppm by mass, Re (Re equivalent)=470 ppm by mass, and Mo (Mo equivalent)=190 ppm by mass. That is, weight ratio of rhenium (Re) content to molybdenum (Mo) content was about 2.5 (=470/190), and rhenium content (rhenium equivalent) was 505 ppm per 1 $m^2/g$ of carrier specific surface area.

Comparative Example 4

Preparation of Catalyst L

Hereinafter, procedures for preparing catalyst L are shown. Catalyst (L) was obtained in the same way as the method described in Example 7, except that carrier L (α-alumina carrier, specific surface area=1.64 $m^2/g$, $SiO_2$ content=0.69% by mass, $Na_2O$=0.03% by mass, water absorption rate=39.5%, pore volume=0.40 ml/g, average pore diameter=0.91 μm) was used.

Content of each component of thus obtained catalyst (L) (based on mass of the catalyst) was as follows: Ag (silver equivalent)=14.8% by mass, Cs (Cs equivalent)=2110 ppm by mass, Re (Re equivalent)=370 ppm by mass, and Mo (Mo equivalent)=100 ppm by mass. That is, weight ratio of rhenium (Re) content to molybdenum (Mo) content was about 3.7 (=370/100), and rhenium content (rhenium equivalent) was 226 ppm per 1 $m^2/g$ of carrier specific surface area.

[Evaluation of Catalyst Performance 4]

Catalysts (J) to (L) prepared in the above Examples 7 and 8 and Comparative Examples 4 were crushed to 600 to 850 μm, respectively. Subsequently, each crushed catalyst (3.0 g) was packed into an external heating type double-tube style stainless steel reactor having inner diameter of 5 mm and tube length of 300 mm. A gas composed of 23% by volume of ethylene, 7.0% by volume of oxygen, 2.1% by volume of carbon dioxide, 2.6 to 3.2 ppm of ethyl chloride, and the balance of nitrogen was introduced into this packed bed, and reaction was carried out under the conditions of reaction pressure of 1.6 and 2.3 MPa and space velocity of 5500 $hr^{-1}$, so that ethylene conversion rate became 10.9%. It should be noted that selectivity rate (Expression 2) and conversion rate (Expression 3) in the preparation of ethylene oxide were calculated according to Expression 2 and Expression 3 described in Evaluation of catalyst performance 1. Performances under various pressures are shown in the following Table 8. It should be noted that, comparisons of the carriers and the catalyst component are shown in Table 7.

TABLE 7

| | | Carrier | | | | Catalyst component | | | | |
| | | | | | | Cs | Re | Mo | | |
| | Catalyst | Specific surface area [$m^2/g$] | $SiO_2$ content [wt %] | $Na_2O$ content [wt %] | $SiO_2$/ $Na_2O$ | content (based on catalyst) [wtppm] | content (based on catalyst) [wtppm] | content (based on catalyst) [wtppm] | Re content* [wtppm/ ($m^2/g$)] | Re/Mo weight ratio |
|---|---|---|---|---|---|---|---|---|---|---|
| Example 7 | J | 0.85 | 1.91 | 0.19 | 10.1 | 2180 | 360 | 90 | 424 | 4.0 |
| Example 8 | K | 0.93 | 0.65 | 0.12 | 5.4 | 1940 | 470 | 190 | 505 | 2.5 |
| Comparative Example 4 | L | 1.64 | 0.69 | 0.03 | 23.0 | 2110 | 370 | 100 | 226 | 3.7 |

*Re content: Rhenium content (rhenium equivalent) per 1 $m^2/g$ of carrier specific surface area.

TABLE 8

| | | 1.6 MPa | | 2.3 MPa | |
|---|---|---|---|---|---|
| | Catalyst | Selectivity rate [%] | Reaction temperature [° C.] | Selectivity rate [%] | Reaction temperature [° C.] |
| Example 7 | J | 89.9 | 260 | 85.9 | 250 |
| Example 8 | K | 89.1 | 267 | 85.7 | 252 |
| Comparative Example 4 | L | 86.3 | 251 | 85.2 | 245 |

The invention claimed is:

1. A catalyst for producing ethylene oxide having a catalyst component (B) supported on a carrier (A) containing α-alumina as a main component, wherein the carrier (A) has a specific surface area of 0.5 to 1.3 m$^2$/g, a Si content (SiO$_2$ equivalent) of 0.1 to 5.0% by mass, and a Na content (Na$_2$O equivalent) of 0.05 to 1.0% by mass, a mass ratio of the Na content (Na$_2$O equivalent) to the Si content (SiO$_2$ equivalent) (Na$_2$O/SiO$_2$) being 1-100, and the catalyst component (B) is silver (Ag), cesium (Cs), rhenium (Re), and tungsten (W), and/or molybdenum (Mo), a weight ratio of Re to W being in the range of 1.1-3.0 and a weight ratio of Re to Mo being in the range of 2.5-4.0, and a cesium (Cs) content being 1000-4000 ppm relative to the total mass of the catalyst.

2. The catalyst for producing ethylene oxide according to claim 1, wherein the rhenium content (rhenium equivalent) is 200 to 1500 ppm per 1 m$^2$/g of the carrier specific surface area.

3. A method for producing ethylene oxide, wherein ethylene is subjected to gas phase oxidation by a molecular-oxygen-containing gas in the presence of the catalyst according to claim 1.

4. A method for producing ethylene oxide, wherein ethylene is subjected to gas phase oxidation by a molecular-oxygen-containing gas in the presence of the catalyst according to claim 2.

5. A method for producing ethylene oxide, wherein ethylene is subjected to gas phase oxidation by a molecular-oxygen-containing gas in the presence of the catalyst according to claim 1 and a weight ratio of rhenium (Re) to tungsten (W) or molybdenum (Mo) (ratio converted to rhenium/tungsten or molybdenum) is 0.4 or more and less than 5.0.

6. A method for producing ethylene oxide, wherein ethylene is subjected to gas phase oxidation by a molecular-oxygen-containing gas in the presence of the catalyst according to claim 2 and a weight ratio of rhenium (Re) to tungsten (W) or molybdenum (Mo) (ratio converted to rhenium/tungsten or molybdenum) is 0.4 or more and less than 5.0.

7. The catalyst for producing ethylene oxide according to claim 1, wherein the α-alumina content is at least 70% by mass the carrier (A), and the cesium content to the total mass of the catalyst is 400-7000 ppm.

8. The catalyst for producing ethylene oxide according to claim 1 or 2, wherein the α-alumina content is at least 70% by mass the carrier (A), and the cesium content to the total mass of the catalyst is 400-4000 ppm.

9. The catalyst for producing ethylene oxide according to claim 1, wherein the tungsten (W) content to the carrier (A) is 40-1200 ppm.

* * * * *